(12) United States Patent
Rein

(10) Patent No.: US 11,009,499 B2
(45) Date of Patent: May 18, 2021

(54) METHOD AND APPARATUS FOR DETERMINING PROPERTIES OF A LABORATORY SAMPLE CONTAINED IN A LABORATORY SAMPLE CONTAINER BY TOMOGRAPHIC RECONSTRUCTION

(71) Applicant: Roche Diagnostics Operations, Inc., Indianapolis, IN (US)

(72) Inventor: Michael Rein, Fellbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 8 days.

(21) Appl. No.: 15/996,898

(22) Filed: Jun. 4, 2018

(65) Prior Publication Data

US 2018/0356392 A1    Dec. 13, 2018

(30) Foreign Application Priority Data

Jun. 9, 2017    (EP) ................................. 17175373

(51) Int. Cl.
*G01N 33/49* (2006.01)
*G01N 15/14* (2006.01)
(Continued)

(52) U.S. Cl.
CPC ............. *G01N 33/49* (2013.01); *G01N 15/06* (2013.01); *G01N 15/1434* (2013.01);
(Continued)

(58) Field of Classification Search
CPC .. G01N 33/49; G01N 15/1434; G01N 33/491;
G01N 21/17; G01N 15/06; G01N 15/1463; G01N 2201/0662; G01N 2015/0092; G01N 2015/0065; G01N 2015/0693; G01N 2015/1006; G01N 2021/1787; G01N 21/94; G01N 21/59
See application file for complete search history.

(56) References Cited

U.S. PATENT DOCUMENTS 4,580,219 A  *  4/1986  Pelc ...................... G06T 11/005
                                                    382/131
5,447,159 A  *  9/1995  Schultz ................ A61B 5/0091
                                                    250/358.1

(Continued)

FOREIGN PATENT DOCUMENTS

EP        2770318 A1    8/2014
JP     2006-010453 A    1/2006
(Continued)

OTHER PUBLICATIONS

European Search Report issued Nov. 16, 2017, in Application No. Ep 17175373.4, 2 pp.

*Primary Examiner* — Michael P LaPage
(74) *Attorney, Agent, or Firm* — Roche Diagnostics Operations, Inc.

(57) ABSTRACT

A method for determining properties of a laboratory sample contained in a laboratory sample container is presented. The method comprises measuring projections of the laboratory sample container comprising the laboratory sample by irradiating light to the laboratory sample container at different projection angle and determining the properties by tomographic reconstruction based on the projections.

2 Claims, 1 Drawing Sheet

(51) Int. Cl.
*G01N 15/06* (2006.01)
*G01N 21/17* (2006.01)
*G01N 21/94* (2006.01)
*G01N 15/10* (2006.01)
*G01N 15/00* (2006.01)

(52) U.S. Cl.
CPC ......... *G01N 15/1463* (2013.01); *G01N 21/17* (2013.01); *G01N 33/491* (2013.01); *G01N 21/94* (2013.01); *G01N 2015/0065* (2013.01); *G01N 2015/0092* (2013.01); *G01N 2015/0693* (2013.01); *G01N 2015/1006* (2013.01); *G01N 2021/1787* (2013.01); *G01N 2201/0662* (2013.01)

(56) References Cited

U.S. PATENT DOCUMENTS

| | | | |
|---|---|---|---|
| 2003/0199758 A1* | 10/2003 | Nelson | G01N 15/1475 600/425 |
| 2004/0076319 A1* | 4/2004 | Fauver | G01N 15/1468 382/133 |
| 2005/0189494 A1* | 9/2005 | Conwell | G01T 1/20 250/363.04 |
| 2006/0182327 A1* | 8/2006 | Mundy | G06K 9/00503 382/132 |
| 2008/0285823 A1* | 11/2008 | Bakker | G01N 21/4795 382/128 |
| 2009/0324047 A1* | 12/2009 | Jarisch | G06T 11/006 382/131 |
| 2010/0158194 A1* | 6/2010 | Pack | A61B 6/032 378/98.12 |
| 2012/0017482 A1* | 1/2012 | Chvala | F41C 23/16 42/71.01 |
| 2012/0307962 A1* | 12/2012 | Cho | A61P 43/00 378/6 |
| 2013/0303898 A1* | 11/2013 | Kinahan | A61B 6/5264 600/425 |
| 2014/0085623 A1* | 3/2014 | Lorbeer | G01N 21/4795 356/51 |
| 2014/0328453 A1* | 11/2014 | Hsieh | A61B 6/035 378/16 |
| 2015/0157286 A1* | 6/2015 | Wang | A61B 6/485 600/426 |
| 2016/0299593 A1* | 10/2016 | Christiansson | G06F 3/042 |
| 2017/0301101 A1* | 10/2017 | Stoppe | G06T 11/003 |
| 2018/0144515 A1* | 5/2018 | Jarisch | G06T 11/008 |
| 2018/0353147 A1* | 12/2018 | Wang | A61B 6/481 |
| 2020/0058140 A1* | 2/2020 | Meldrum | G01N 15/1434 |

FOREIGN PATENT DOCUMENTS

| | | |
|---|---|---|
| JP | 2010-256361 A | 11/2010 |
| WO | 2003/098539 A1 | 11/2003 |
| WO | 2010/135592 A2 | 11/2010 |
| WO | 2014/124057 A1 | 8/2014 |
| WO | 2015/002218 A1 | 1/2015 |
| WO | 2016/020684 A1 | 2/2016 |
| WO | WO-2016041813 A1 * | 3/2016 ........... G06T 11/003 |
| WO | 2016/131498 A1 | 8/2016 |

\* cited by examiner

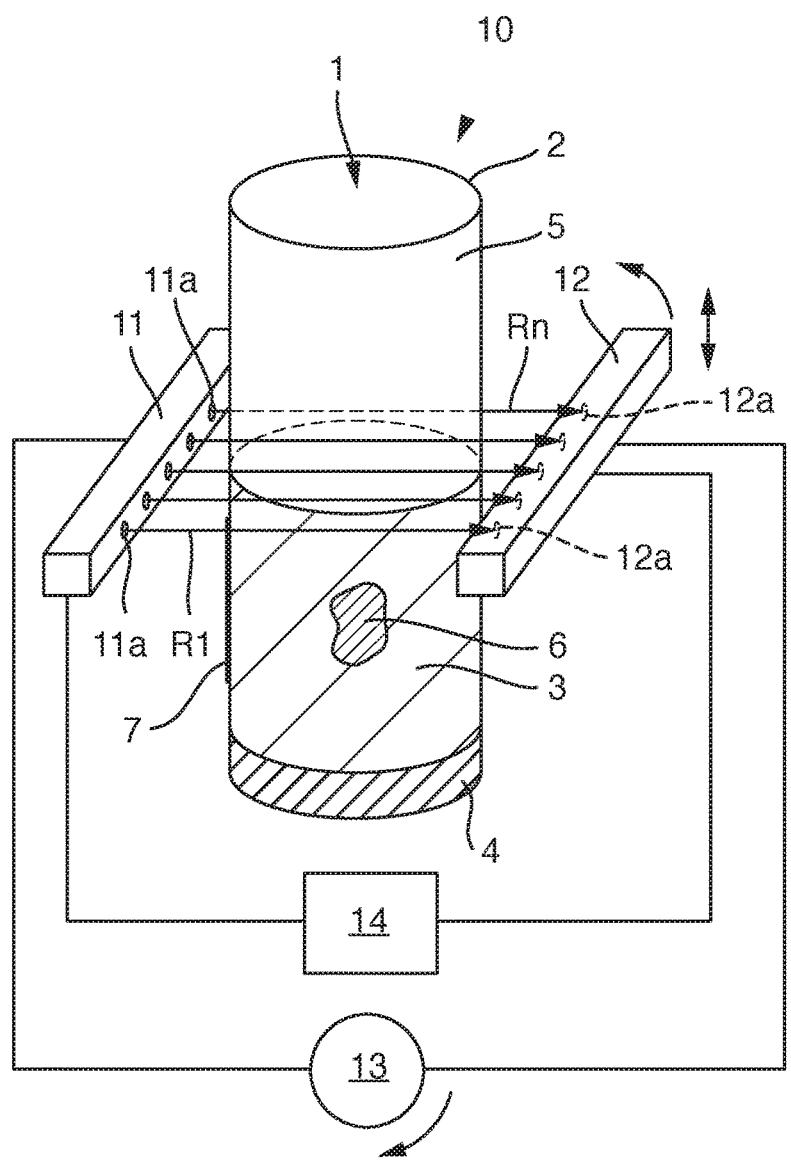
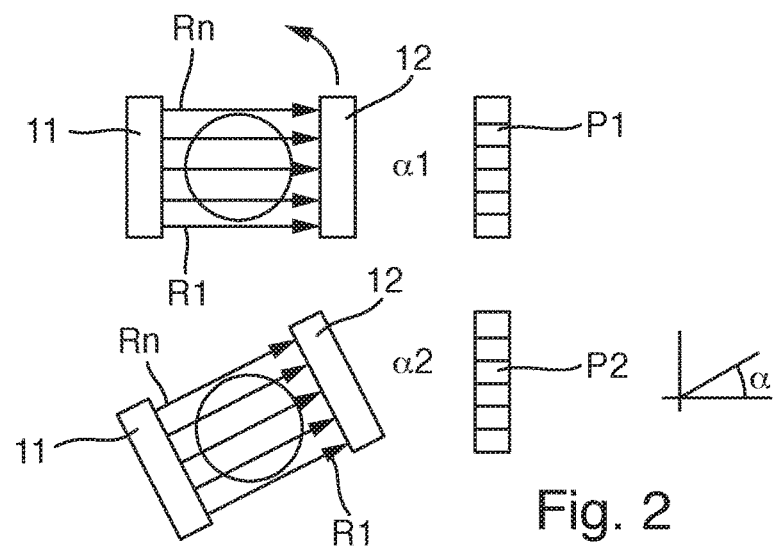
Fig. 1
Fig. 2

METHOD AND APPARATUS FOR DETERMINING PROPERTIES OF A LABORATORY SAMPLE CONTAINED IN A LABORATORY SAMPLE CONTAINER BY TOMOGRAPHIC RECONSTRUCTION

CROSS-REFERENCE TO RELATED APPLICATIONS

This application claims the benefit of EP 17175373.4, filed Jun. 9, 2017, which is hereby incorporated by reference.

BACKGROUND

The present disclosure relates to a method and an apparatus for determining properties of a laboratory sample contained in a laboratory sample container.

In the technical field of laboratory automation laboratory sample containers comprising centrifuged blood samples may have to be processed. The blood samples may be separated into serum and cruor (blood cells) by a separating medium. If, for example, an aliquot of the serum has to be generated, part of the serum has to be transferred to another sample container, e.g. by a pipette device. If impurities such as, for example, in the form of foreign matter, are present in the serum, the pipette device may not function properly, since the impurities may block or close an opening of the pipette device.

Typically, labels comprising sample related information are placed on the laboratory sample container. These labels complicate the process of optically detecting properties of the laboratory sample.

Therefore, there is a need for a method and an apparatus for determining properties of a laboratory sample contained in a laboratory sample container providing reliable results in determining the properties, even if labels are placed on the laboratory sample container.

SUMMARY

According to the present disclosure, a method for determining properties of a laboratory sample contained in a laboratory sample container is presented. The method can comprise measuring projections (P1, P2) of the laboratory sample container comprising the laboratory sample by irradiating light to the laboratory sample container at different projection angles ($\alpha 1$, $\alpha 2$) and determining the properties by tomographic reconstruction based on the projections (P1, P2).

In accordance with one embodiment of the present disclosure, an apparatus for determining properties of a laboratory sample contained in a laboratory sample container is presented. The apparatus can be configured to perform the method of claim 1. The apparatus can comprise a light source for irradiating light to the laboratory sample container such that the light passes through the laboratory sample container and the laboratory sample, a light detector for determining projections (P1, P2) by measuring an intensity of light being based on the irradiated light and exiting the laboratory sample container, a rotating drive for rotating the light source and the light detector relative to the sample container to effect different projection angles ($\alpha 1$, $\alpha 2$), and a processor for determining the properties by tomographic reconstruction based on the projections (P1, P2).

Accordingly, it is a feature of the embodiments of the present disclosure to provide a method and an apparatus for determining properties of a laboratory sample contained in a laboratory sample container providing reliable results in determining the properties, even if labels are placed on the laboratory sample container. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1 illustrates schematically an apparatus for determining properties of a laboratory sample contained in a laboratory sample container in a perspective view according to an embodiment of the present disclosure.

FIG. 2 illustrates schematically the apparatus of FIG. 1 in a top view in two different projection angles according to an embodiment of the present disclosure.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The method for determining properties of a laboratory sample contained in a laboratory sample container can be based on a tomographic measurement process including tomographic reconstruction. Regarding the fundamentals of the tomographic measurement process including tomographic reconstruction reference is made to the relevant technical literature known in the art.

The method can comprise measuring projections of the laboratory sample container comprising the laboratory sample by irradiating light to the laboratory sample container at different projection angles. A projection of an object, here an object in form of the laboratory sample container comprising the laboratory sample, can result from the tomographic measurement process at a given projection angle. The projection can typically be made up of a set of line integrals. The projections may be represented by a vector. Elements of the vector can be formed by the line integrals e.g. in a binary representation.

An intensity of light irradiated to the laboratory sample container can be chosen such that a sufficient quantity of light can pass through the laboratory sample container, even if a label is placed on the laboratory sample container. A wavelength of the light may, for example, be chosen in the visible or infrared wavelength range.

The method can further comprise determining the properties by tomographic reconstruction based on the projections. The properties may, for example, be embodied as a cross sectional image of the laboratory sample container and of the laboratory sample. The image may, for example, be formed by discrete pixels.

Due to the above method, the properties of the sample may be reliably determined, even if labels are placed on the laboratory sample container. Further, a cross sectional image of the laboratory sample may be obtained making it possible to detect impurities in the laboratory sample.

The above described method steps may be repeated for a number of different vertical positions in order to obtain a number of cross sectional images of the laboratory sample container and of the laboratory sample at the different vertical positions.

According to an embodiment, measuring the projections can comprise: irradiating light to the laboratory sample container, such that the light can pass through the laboratory sample container and the laboratory sample, and measuring an intensity of light exiting the laboratory sample container. The light exiting the laboratory sample container can be based on the irradiated light.

According to an embodiment, light can be irradiated to the laboratory sample container in the form of substantially parallel light rays or beams at the respective projection angles. The substantially parallel light rays or beams may be located in a horizontal projection plane being substantially perpendicular to an axis of the laboratory sample container. Accordingly, the light exiting the laboratory sample container may be measured in the projection plane.

According to an embodiment, the projections made under the different projection angles can form a sinogram. Reference is made insofar also to the relevant technical literature.

According to an embodiment, the tomographic reconstruction can be based on the Radon Transformation and/or a Fourier-Domain Reconstruction Algorithm and/or a Filtered Back Projection Algorithm and/or an Iterative Reconstruction Algorithm and/or Fan-Beam Reconstruction and/or spiral computed tomography. Reference is made insofar to the relevant technical literature.

According to an embodiment, the properties of the laboratory sample can be the light attenuation coefficients of the laboratory sample as a function of a position or location inside the laboratory sample container.

According to an embodiment, the laboratory sample can be a centrifuged blood sample. The blood sample can be separated into serum and at least one other component. The at least one other component may, for example, be embodied as cruor (blood cells), a separating medium (gel) or air.

According to an embodiment, foreign matter in the serum may be detected based on the determined properties. The foreign matter may, for example, be embodied as a clot typically comprising afibrinogenaemia fibers, coagulum, fat/protein agglutination or the like.

According to an embodiment, properties of labels attached to the laboratory sample container may be determined based on the determined properties. The properties of labels may, for example, be if a label is placed on the laboratory sample container, an extension of the label placed on the laboratory sample container, a thickness of the label and/or a number of layers of the label.

According to an embodiment, the laboratory sample can be classified based on the determined properties. Typical classes which can be assigned to a laboratory sample such as, for example, in the form of a blood plasma sample such as, for example, a lipemic class, a hemolytic class, an icteric class and a good class. The "good" class can contain those samples which may not be assigned to the class lipemic, hemolytic or icteric. When the sample is to be assigned to the lipemic class, it can be a lipemic sample which can have an elevated level of lipids. This may, for example, be an indication of a disorder of the fat metabolism. When the sample is to be assigned to the hemolytic class, it can be a hemolytic sample which can have an elevated level of hemoglobin. This may, for example, be an indication of particular anemias, transfusion reactions or malaria. When the blood plasma sample is to be assigned to the icteric class, it can be an icteric sample which can have an elevated level of bilirubin. This may, for example, be an indication of a disease of the liver.

The apparatus for determining properties of a laboratory sample contained in a laboratory sample container can be configured to perform the method as described above.

According to an embodiment, a liquid level of the laboratory sample comprised in the laboratory sample container can be determined based on the determined properties.

According to an embodiment, a rough cell analysis can be performed based on the determined properties.

The apparatus, for example, forming a laboratory diagnostic device, can comprise a light source for irradiating light to the laboratory sample container, such that the light can pass through the laboratory sample container and the laboratory sample. The light source may, for example, be embodied as a number (e.g., 10 to 100) of linearly arranged laser diodes irradiating light in form of substantially parallel rays at the respective projection angles. The laser diodes may be linearly arranged in a horizontal projection plane being substantially perpendicular to an axis of the laboratory sample container.

The apparatus can further comprise a light detector for measuring an intensity of light being based on the irradiated light exiting the laboratory sample container. The light detector may, for example, be embodied as a number (e.g., 10 to 100) of linearly arranged photo detectors. The photo detectors may be linearly arranged in the horizontal projection plane horizontally spaced from the laser diodes, such that the sample container can be placed between the laser diodes and the photo detector.

The apparatus can further comprise a rotating drive for rotating the light source together with the light detector relative to the sample container to cause different projection angles.

The apparatus further can comprise a numeric processor for determining the properties by tomographic reconstruction based on the projections.

Referring initially to FIG. 1, FIG. 1 schematically depicts an apparatus 10 for determining properties of a laboratory sample 1 contained in a laboratory sample container 2. The properties of the laboratory sample 1 can be the light attenuation coefficients of the laboratory sample 1 in a projection plane.

The laboratory sample 1 can be a centrifuged blood sample. The blood sample 1 can be separated into cruor 4, serum 3 and air 5. The blood sample 1 may contain foreign matter 6 in the serum 3 in form of a clot. Further, a label 7 comprising sample related information can be attached to the laboratory sample container 2.

The apparatus 10 can comprise a light source 11 in the form of a linear array of a number n of laser diodes 11a for irradiating light to the laboratory sample container 2, such that the light can pass through the laboratory sample container 2 and the laboratory sample 1 in the form of substantially parallel rays R1 to Rn.

The apparatus 10 can further comprise a light detector 12 for determining projections forming a sinogram by measuring an intensity of light exiting the laboratory sample container 2 and being based on the irradiated light. The light detector 12 can be formed by a linear array of n photo detectors 12a, e.g. in form of photo diodes.

The number n of laser diodes 11a and photo detectors 12a, respectively, for example, may lie in the range between 4 and 100.

The laser diodes 11a and the photo detectors 12a can be placed opposite to one another in a common projection plane. The sample container 2 can be placed between the laser diodes 11a and the photo detectors 12a. The projection plane can be substantially perpendicular to an axis of the sample container 2.

The apparatus 10 can further comprise a rotating drive 13 for rotating the light source 11 and the light detector 12 relative to the sample container 2 to effect different projection angles α1 and α2, see FIG. 2.

The apparatus 10 can further comprise a processor 14 for determining the properties by tomographic reconstruction based on the projections P1 and P2.

Now also referring to FIG. 2, the apparatus 10 can operate as follows.

Using the laser diodes 11a, light in the form of substantially parallel light beams or rays R1 to Rn can be irradiated to the laboratory sample container 2 at a first projection angle α1, such that the light can pass through the laboratory sample container 2 and the laboratory sample 1. Using the photo detectors 12a, an intensity of light based on the irradiated light exiting the laboratory sample container 2 can be measured. A projection P1 can be formed by the different measured values of the photo detectors 12a.

If the projection P1 is generated, the rotating drive 13 can rotate the light source 11 and the light detector 12 relative to the sample container 2 to effect the projection angle α2 and the above steps can be repeated to generate the projection P2.

Self-evidently, typically more than the two exemplarily depicted projections P1 and P2 at the respective projection angles α1 and α2 can be used to determine the properties. For example, a number of about 15 to about 180 projections covering an angle range of approximately 180 angular degrees may be used to determine the properties.

If the projections are determined, the processor 14 can determine the properties by tomographic reconstruction based on the projections P1 and P2. The tomographic reconstruction may be based on the Radon Transformation and/or a Fourier-Domain Reconstruction Algorithm and/or a Filtered Back Projection Algorithm and/or an Iterative Reconstruction Algorithm and/or Fan-Beam Reconstruction and/or spiral computed tomography.

The above described steps can then be repeated for different vertical levels, e.g. covering the complete vertical extension of the serum 3.

By use of the apparatus and method, the properties of the laboratory sample 1 in the form of the light attenuation coefficients of the laboratory sample 1 in the projection plane can be evaluated. The properties may be represented in form of a digital image composed of pixels representing the corresponding light attenuation coefficients in the projection plane. Thus, the extent of the clot 6 in the projection plane for all measured vertical levels may be determined, even if a label 7 is placed on the laboratory sample container 2.

The pixel resolution can typically depend on the number n of laser diodes 11a and photo detectors 12a.

Further, the laboratory sample 1 may be classified based on the light attenuation coefficients, since the light attenuation coefficients can be, for example, specific for lipemic, hemolytic class, and/or an icteric sample.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method for determining properties of a laboratory sample contained in a laboratory sample container, wherein the laboratory sample is a centrifuged blood sample, the method comprising:
    measuring projections (P1, P2) of the laboratory sample container comprising the laboratory sample by irradiating light to the laboratory sample container at different projection angles (α1, α2), wherein the light is irradiated in form of parallel rays (R1 to Rn) at the respective projection angles (α1, α2), wherein the projections (P1, P2) form a sonogram, and wherein the irradiated light has a wavelength chosen from the visible or infrared wavelength range;
    determining the properties by tomographic reconstruction based on the projections (P1, P2), wherein the properties are the light attenuation coefficients of the laboratory sample as a function of a position inside the laboratory sample container;
    separating the centrifuged blood sample into serum and at least one other component; and
    detecting foreign matter in the serum based on the determined properties.

2. The method according to claim 1, wherein the measurement of the projections (P1, P2) comprises irradiating light to the laboratory sample container, such that the light passes through the laboratory sample container and the laboratory sample, and measuring an intensity of light being based on the irradiated light exiting the laboratory sample container.

* * * * *